(12) United States Patent
Bolin et al.

(10) Patent No.: US 8,211,884 B2
(45) Date of Patent: Jul. 3, 2012

(54) DIACYLGLYCEROL ACYLTRANSFERASE INHIBITORS

(75) Inventors: David Robert Bolin, Montclair, NJ (US); Stuart Hayden, Manalapan, NJ (US); Yimin Qian, Wayne, NJ (US)

(73) Assignee: Madrigal Pharmaceuticals, Inc., Fort Washington, PA (US)

( * ) Notice: Subject to any disclaimer, the term of this patent is extended or adjusted under 35 U.S.C. 154(b) by 406 days.

(21) Appl. No.: 12/507,890

(22) Filed: Jul. 23, 2009

(65) Prior Publication Data
US 2010/0035864 A1 Feb. 11, 2010

Related U.S. Application Data

(60) Provisional application No. 61/086,506, filed on Aug. 6, 2008.

(51) Int. Cl.
  A61P 3/00    (2006.01)
  A61K 31/5513 (2006.01)
  C07D 413/02  (2006.01)
  C07D 413/14  (2006.01)
(52) U.S. Cl. .................. 514/218; 540/597; 540/603
(58) Field of Classification Search .......... 514/218; 540/597, 603
See application file for complete search history.

(56) References Cited

U.S. PATENT DOCUMENTS

| | | | |
|---|---|---|---|
| 3,250,771 A | 5/1966 | Leonard et al. |
| 3,929,793 A | 12/1975 | Popelak et al. |
| 4,066,654 A | 1/1978 | Adelstein et al. |
| 7,015,218 B1 | 3/2006 | Ushio et al. |
| 7,094,896 B2 | 8/2006 | Ding et al. |
| 7,148,246 B2 | 12/2006 | Gretzke et al. |
| 7,160,911 B2 | 1/2007 | Goerlitzer et al. |
| 7,244,727 B2 | 7/2007 | Fox et al. |
| 7,317,125 B2 | 1/2008 | Bolin et al. |
| 7,714,126 B2 | 5/2010 | Bolin et al. |
| 8,058,299 B2 | 11/2011 | Bolin et al. |
| 8,115,011 B2 | 2/2012 | Bolin et al. |
| 2004/0019067 A1 | 1/2004 | Armistead et al. |
| 2007/0123504 A1 | 5/2007 | Bolin et al. |
| 2009/0093497 A1 | 4/2009 | Bolin et al. |
| 2009/0099201 A1 | 4/2009 | Bolin et al. |
| 2009/0105273 A1 | 4/2009 | Bolin et al. |
| 2009/0170864 A1 | 7/2009 | Bolin et al. |
| 2010/0113782 A1 | 5/2010 | Bolin et al. |
| 2010/0145047 A1 | 6/2010 | Bolin et al. |
| 2010/0152445 A1 | 6/2010 | Bolin et al. |

FOREIGN PATENT DOCUMENTS

| | | |
|---|---|---|
| AU | 2002333456 A2 | 3/2003 |
| CA | 2458210 | 3/2003 |
| EP | 1535915 A1 | 6/2005 |
| WO | WO-0047558 A1 | 8/2000 |
| WO | 03020269 | 3/2003 |
| WO | WO-2006134317 A1 | 12/2006 |
| WO | WO-2007060140 A2 | 5/2007 |
| WO | 2007141538 | 12/2007 |
| WO | WO-2008141976 A1 | 11/2008 |
| WO | WO-2010065310 A1 | 6/2010 |
| WO | WO-2010077861 A1 | 7/2010 |

OTHER PUBLICATIONS

Labute et al, "A Probabilistic Approach to High Throughput Drug Discovery," Comb Chem. High Throughput Screen., 2002, 5(2):135-145.
The International Search Report and Written Opinion by the International Searching Authority, issued on Sep. 15, 2009, in the PCT application No. PCT/US09/51614.

*Primary Examiner* — Brenda Coleman
(74) *Attorney, Agent, or Firm* — Mintz Levin Cohn Ferris Glovsky and Popeo, P.C.; Ivor R. Elrifi; Heidi A. Erlacher

(57) ABSTRACT

Provided herein are compounds of the formula (I):

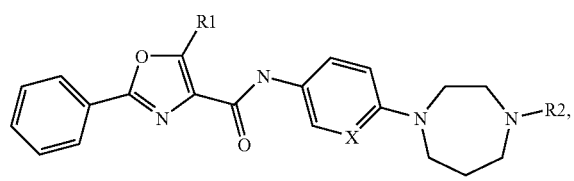

as well as pharmaceutically acceptable salts thereof, wherein the substituents are as those disclosed in the specification. These compounds, and the pharmaceutical compositions containing them, are useful for the treatment of diseases such as, for example, obesity, type II diabetes mellitus and metabolic syndrome.

15 Claims, No Drawings

DIACYLGLYCEROL ACYLTRANSFERASE INHIBITORS

CROSS-REFERENCE TO RELATED APPLICATIONS

This application claims priority from U.S. Provisional Application No. 61/086,506 filed on Aug. 6, 2008. The above mentioned application is incorporated herein by reference.

FIELD OF THE INVENTION

The invention involves inhibitors of diacylglycerol acyltransferase. The inhibitors are useful for the treatment of diseases such as obesity, type II diabetes mellitus, dyslipidemia and metabolic syndrome.

All documents cited or relied upon below are expressly incorporated herein by reference.

BACKGROUND OF THE INVENTION

Triglycerides or triacylglycerols are the major form of energy storage in eukaryotic organisms. In mammals, these compounds are primarily synthesized in three tissues: the small intestine, liver, and adipocytes. Triglycerides or triacylglycerols support the major functions of dietary fat absorption, packaging of newly synthesized fatty acids and storage in fat tissue (see Subauste and Burant, Current Drug Targets—Immune, Endocrine & Metabolic Disorders (2003) 3, 263-270).

Diacylglycerol O-acyltransferase, also known as diglyceride acyltransferase or DGAT, is a key enzyme in triglyceride synthesis. DGAT catalyzes the final and rate-limiting step in triacylglycerol synthesis from 1,2-diacylglycerol (DAG) and long chain fatty acyl CoA as substrates. Thus, DGAT plays an essential role in the metabolism of cellular diacylglycerol and is critically important for triglyceride production and energy storage homeostasis (see Mayorek et al, European Journal of Biochemistry (1989) 182, 395-400).

DGAT has a specificity for sn-1,2 diacylglycerols and will accept a wide variety of fatty acyl chain lengths (see Farese et al, Current Opinions in Lipidology (2000) 11, 229-234). DGAT activity levels increase in fat cells as they differentiate in vitro and recent evidence suggests that DGAT may be regulated in adipose tissue post-transcriptionally (see Coleman et al, Journal of Molecular Biology (1978) 253, 7256-7261 and Yu et al, Journal of Molecular Biology (2002) 277, 50876-50884). DGAT activity is primarily expressed in the endoplasmic reticulum (see Colman, Methods in Enzymology (1992) 209, 98-104). In hepatocytes, DGAT activity has been shown to be expressed on both the cytosolic and luminal surfaces of the endoplasmic reticular membrane (see Owen et al, Biochemical Journal (1997) 323 (pt 1), 17-21 and Waterman et al, Journal of Lipid Research (2002) 43, 1555-156). In the liver, the regulation of triglyceride synthesis and partitioning, between retention as cytosolic droplets and secretion, is of primary importance in determining the rate of VLDL production (see Shelness and Sellers, Current Opinions in Lipidology (2001) 12, 151-157 and Owen et al, Biochemical Journal (1997) 323 (pt 1), 17-21).

Two forms of DGAT have been cloned and are designated DGAT1 and DGAT2 (see Cases et al, Proceedings of the National Academy of Science, USA (1998) 95, 13018-13023, Lardizabal et al, Journal of Biological Chemistry (2001) 276, 38862-38869 and Cases et al, Journal of Biological Chemistry (2001) 276, 38870-38876). Although both enzymes utilize the same substrates, there is no homology between DGAT1 and DGAT2. Both enzymes are widely expressed however some differences do exist in the relative abundance of expression in various tissues.

The gene encoding mouse DGAT1 has been used to create DGAT knock-out. These mice, although unable to express a functional DGAT enzyme (Dgat−/− mice), are viable and continue to synthesize triglycerides (see Smith et al, Nature Genetics (2000) 25, 87-90). This would suggest that multiple catalytic mechanisms contribute to triglyceride synthesis, such as DGAT2. An alternative pathway has also been shown to form triglycerides from two diacylglycerols by the action of diacylglycerol transacylase (see Lehner and Kuksis, Progress in Lipid Research (1996) 35, 169-210).

Dgat−/− mice are resistant to diet-induced obesity and remain lean. When fed a high fat diet, Dgat−/− mice maintain weights comparable to mice fed a diet with regular fat content. Dgat−/− mice have lower tissue triglyceride levels. The resistance to weight gain seen in the knockout mice, which have a slightly higher food intake, is due to an increased energy expenditure and increased sensitivity to insulin and leptin (see Smith et al, Nature Genetics (2000) 25, 87-90, Chen and Farese, Trends in Cardiovascular Medicine (2000) 10, 188-192, Chen and Farese, Current Opinions in Clinical Nutrition and Metabolic Care (2002) 5, 359-363 and Chen et al, Journal of Clinical Investigation (2002) 109, 1049-1055). Dgat−/− mice have reduced rates of triglyceride absorption, improved triglyceride metabolism, and improved glucose metabolism, with lower glucose and insulin levels following a glucose load, in comparison to wild-type mice (see Buhman et al, Journal of Biological Chemistry (2002) 277, 25474-25479 and Chen and Farese, Trends in Cardiovascular Medicine (2000) 10, 188-192).

Disorders or imbalances in triglyceride metabolism, both absorption as well as de novo synthesis, have been implicated in the pathogenesis of a variety of disease risks. These include obesity, insulin resistance syndrome, type II diabetes, dyslipidemia, metabolic syndrome (syndrome X) and coronary heart disease (see Kahn, Nature Genetics (2000) 25, 6-7, Yanovski and Yanovski, New England Journal of Medicine (2002) 346, 591-602, Lewis et al, Endocrine Reviews (2002) 23, 201, Brazil, Nature Reviews Drug Discovery (2002) 1, 408, Malloy and Kane, Advances in Internal Medicine (2001) 47, 111, Subauste and Burant, Current Drug Targets—Immune, Endocrine & Metabolic Disorders (2003) 3, 263-270 and Yu and Ginsberg, Annals of Medicine (2004) 36, 252-261). Compounds that can decrease the synthesis of triglycerides from diacylglycerol by inhibiting or lowering the activity of the DGAT enzyme would be of value as therapeutic agents for the treatment of diseases associated with abnormal metabolism of triglycerides.

Known inhibitors of DGAT include: dibenzoxazepinones (see Ramharack, et al, EP1219716 and Burrows et al, 26th National Medicinal Chemistry Symposium (1998) poster C-22), substituted amino-pyrimidino-oxazines (see Fox et al, WO2004047755), chalcones such as xanthohumol (see Tabata et al, Phytochemistry (1997) 46, 683-687 and Casaschi et al, Journal of Nutrition (2004) 134, 1340-1346), substituted benzyl-phosphonates (see Kurogi et al, Journal of Medicinal Chemistry (1996) 39, 1433-1437, Goto, et al, Chemistry and Pharmaceutical Bulletin (1996) 44, 547-551, Ikeda, et al, Thirteenth International Symposium on Atherosclerosis (2003), abstract 2P-0401, and Miyata, et al., JP 2004067635), aryl alkyl acid derivatives (see Smith et al, WO2004100881 and US20040224997), furan and thiophene derivatives (see WO2004022551), pyrrolo[1,2b]pyridazine derivatives (see Fox et al, WO2005103907), substituted sulfonamides (see Budd Haeberlein and Buckett, WO20050442500), thiophenoxyacetamides (see Bolin and Michoud, WO2006082010), arylpropionylhydrazides (see Michoud, WO2006120125) and oxazoledicarboxamides (see Bolin et al, WO2007060140). Most recently, DGAT inhibitors demonstrated efficacy of body weight gain inhibition in obese animal models (Journal of Medicinal Chemistry (2008), 51, 380).

Also known to be inhibitors of DGAT are: 2-bromo-palmitic acid (see Colman et al, Biochimica et Biophysica Acta (1992) 1125, 203-9), 2-bromo-octanoic acid (see Mayorek and Bar-Tana, Journal of Biological Chemistry (1985) 260, 6528-6532), roselipins (see Noriko et al, (Journal of Antibiotics (1999) 52, 815-826), amidepsin (see Tomoda et al, Journal of Antibiotics (1995) 48, 942-7), isochromophilone, prenylflavonoids (see Chung et al, Planta Medica (2004) 70, 258-260), polyacetylenes (see Lee et al, Planta Medica (2004) 70, 197-200), cochlioquinones (see Lee et al, Journal of Antibiotics (2003) 56, 967-969), tanshinones (see Ko et al, Archives of Pharmaceutical Research (2002) 25, 446-448), gemfibrozil (see Zhu et al, Atherosclerosis (2002) 164, 221-228), and substituted quinolones (see Ko, et al, Planta Medica (2002) 68, 1131-1133). Also known to be modulators of DGAT activity are antisense oligonucleotides (see Monia and Graham, US20040185559).

A need exists in the art, however, for additional DGAT inhibitors that have efficacy for the treatment of metabolic disorders such as, for example, obesity, type II diabetes mellitus and metabolic syndrome.

SUMMARY OF THE INVENTION

The present invention pertains to DGAT inhibitors. In a preferred embodiment, the invention provides compounds of the formula (I):

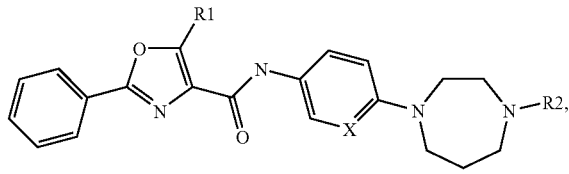

(I)

as well as pharmaceutically acceptable salts thereof and pharmaceutical compositions thereof.

DETAILED DESCRIPTION OF THE INVENTION

In a preferred embodiment of the present invention, provided are compounds of formula (I):

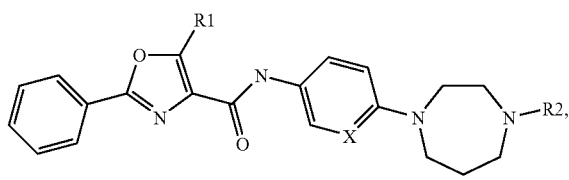

(I)

wherein:
X is C or N;
$R^1$ is lower alkyl substituted with halogen;
$R^2$ is —$CH_2$-aryl, said aryl being unsubstituted or substituted with C(O)OH, or —C(O)—R3;
$R^3$ is -lower alkyl, unsubstituted or substituted with carboxylic acid,
—O-lower alkyl, unsubstituted or substituted with C(O)OH,
—$(CH_2)_n$-cycloalkyl, said cycloalkyl being unsubstituted or substituted with C(O)OH or C(O)O—$CH_2$-phenyl,
—$(CH_2)_n$-aryl, said aryl being unsubstituted or mono- or bi-substituted with C(O)OH,
—N-lower alkyl,
—$(CH_2)_n$-heterocycloalkyl, said heterocycloalkyl being unsubstituted or substituted with (=O), or
—$NH(CH_2)_2C(O)OCH_2Ch_3$; and
n is 0, 1 or 2;
or a pharmaceutically acceptable salt thereof.

In another preferred embodiment of the present invention, provided is a pharmaceutical composition, comprising a therapeutically effective amount of a compound according to formula (I) or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, bornyl, adamantyl, indenyl and the like. In a preferred embodiment, the "cycloalkyl" moieties can optionally be substituted with one, two, three or four substituents, with the understanding that said substituents are not, in turn, substituted further unless indicated otherwise. Each substituent can independently be, for example, alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein. The preferred cycloalkyl radicals are the monocyclic cycloalkyl radicals having from 3 to 6 ring members.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl, thiazolidine-2,4-dione and the like. The heterocycloalkyl groups may be unsubstituted or substituted and attachment may be through their carbon frame or through their heteroatom(s) where appropriate, with the understanding that said substituents are not, in turn, substituted further.

The term "lower alkyl", alone or in combination with other groups, refers to a branched or straight-chain alkyl radical of one to nine carbon atoms, preferably one to six carbon atoms.

This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, napthyl, 1,2,3,4-tetrahydronaphtalene, 1,2-dihydronaphtalene, indanyl, 1H-indenyl and the like, with phenyl being preferred.

The alkyl, loweralkyl and aryl groups may be substituted or unsubstituted. When substituted, there will generally be, for example, 1 to 4 substituents present, with the understanding that said substituents are not, in turn, substituted further unless indicated otherwise. These substituents may optionally form a ring with the alkyl, loweralkyl or aryl group to which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups containing one or more heteroatoms, (e.g. thienyl, furanyl, pyrrolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The heteroaryl group described above may be substituted independently with one, two, or three substituents, with the understanding that said substituents are not, in turn, substituted further unless indicated otherwise. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term "alkoxy" means alkyl-O—; and "alkoyl" means alkyl-CO—. Alkoxy substituent groups or alkoxy-containing substituent groups may be substituted by, for example, one or more alkyl groups, with the understanding that said substituents are not, in turn, substituted further unless indicated otherwise.

As used herein, the term "halogen" means a fluorine, chlorine, bromine or iodine radical, preferably a fluorine, chlorine or bromine radical, and more preferably a fluorine or chlorine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g. intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

Compounds of the present invention can be prepared beginning with commercially available starting materials and utilizing general synthetic techniques and procedures known to those skilled in the art. Outlined below are reaction schemes suitable for preparing such compounds. Further exemplification is found in the specific examples listed below.

Scheme 1

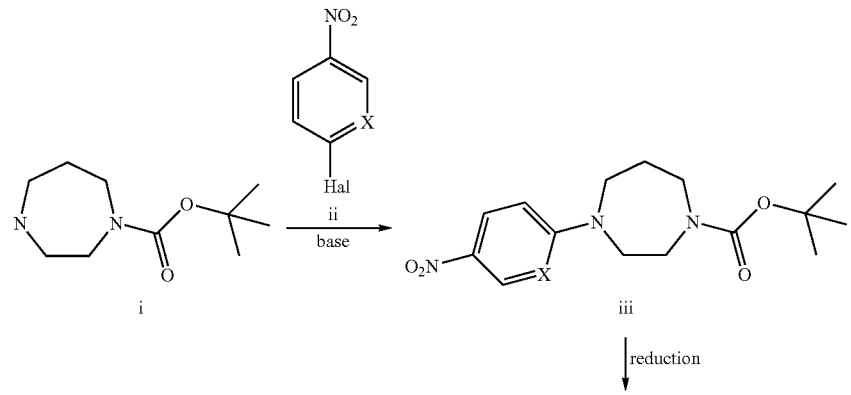

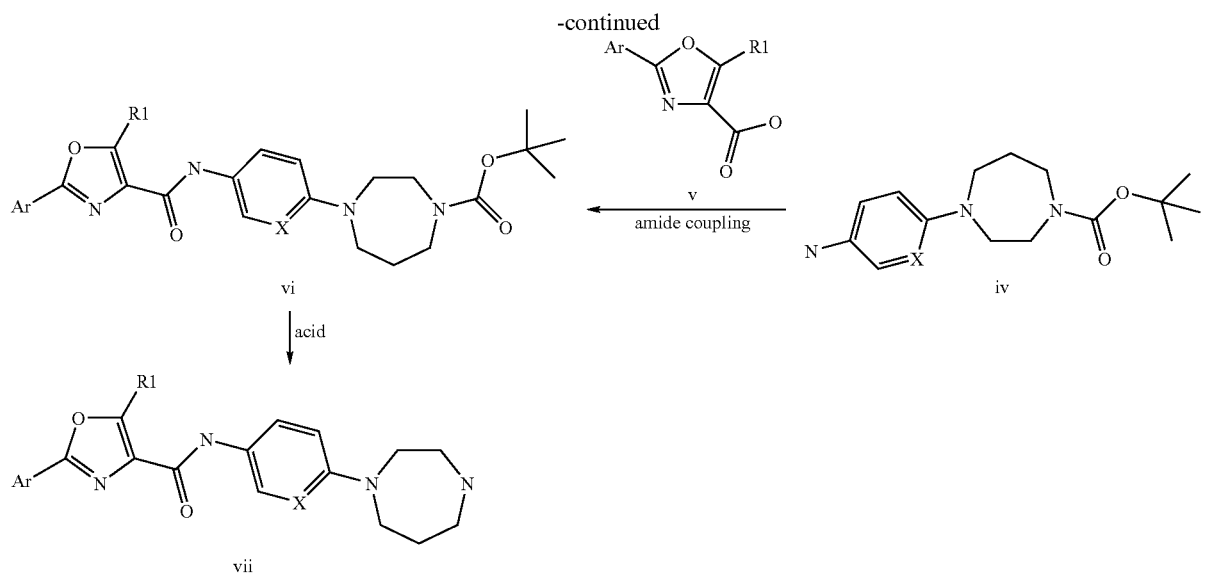

The commercially available diazepane-1-carboxylic acid tert-butyl ester (i) can be reacted with compound (ii) in the presence of base through nucleophilic aromatic substitution, where Hal can be F, Br or Cl and X can be CH or N. The resulting diazepane substituted compound (iii) can be reduced to a corresponding amine (iv). Coupling of amine (iv) with 2-aryl-4-alkyl-oxazole-4-carboxylic acid under amide formation conditions can provide compound (vi). The R1 group in compound (v) can be low alkyl and halogen substituted alkyl, such as trifluoromethyl group. The tert-butyl ester in compound (vi) can be cleaved under acid conditions to give compound (vii).

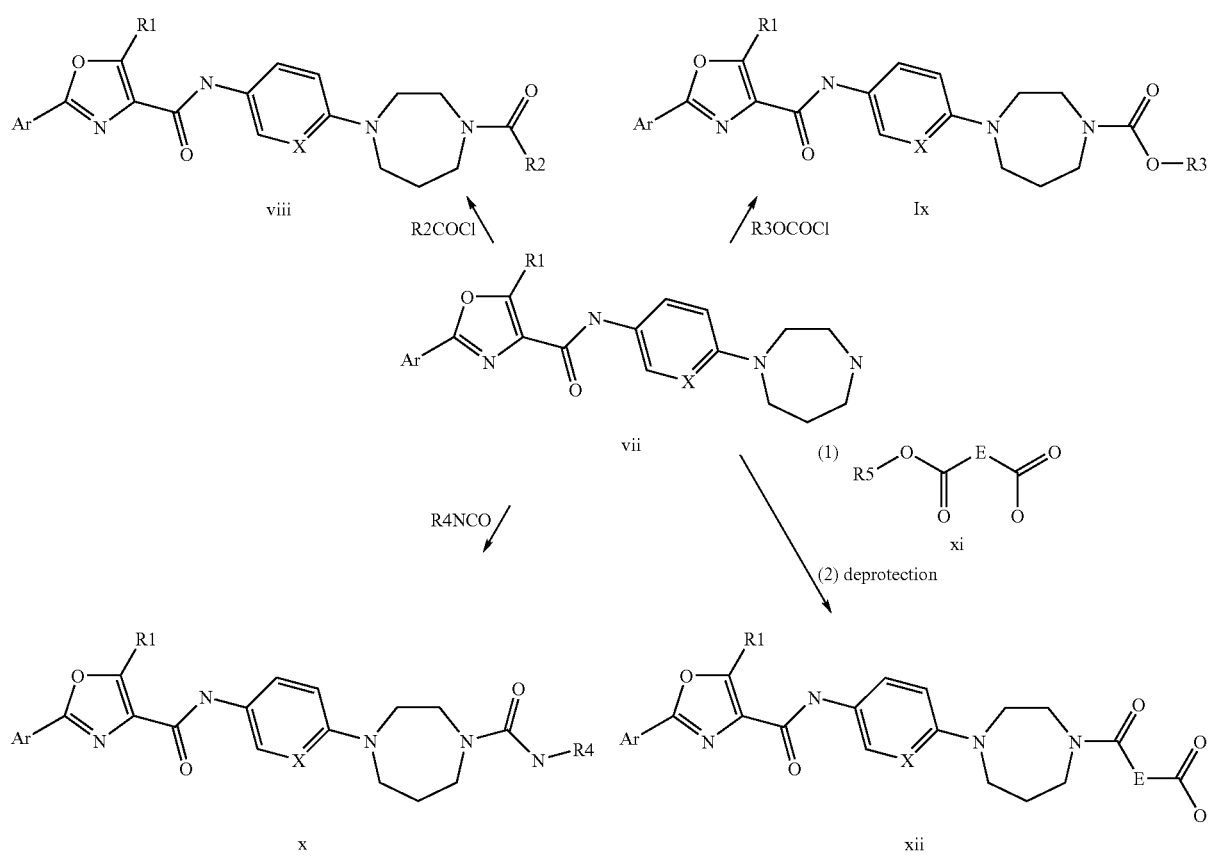

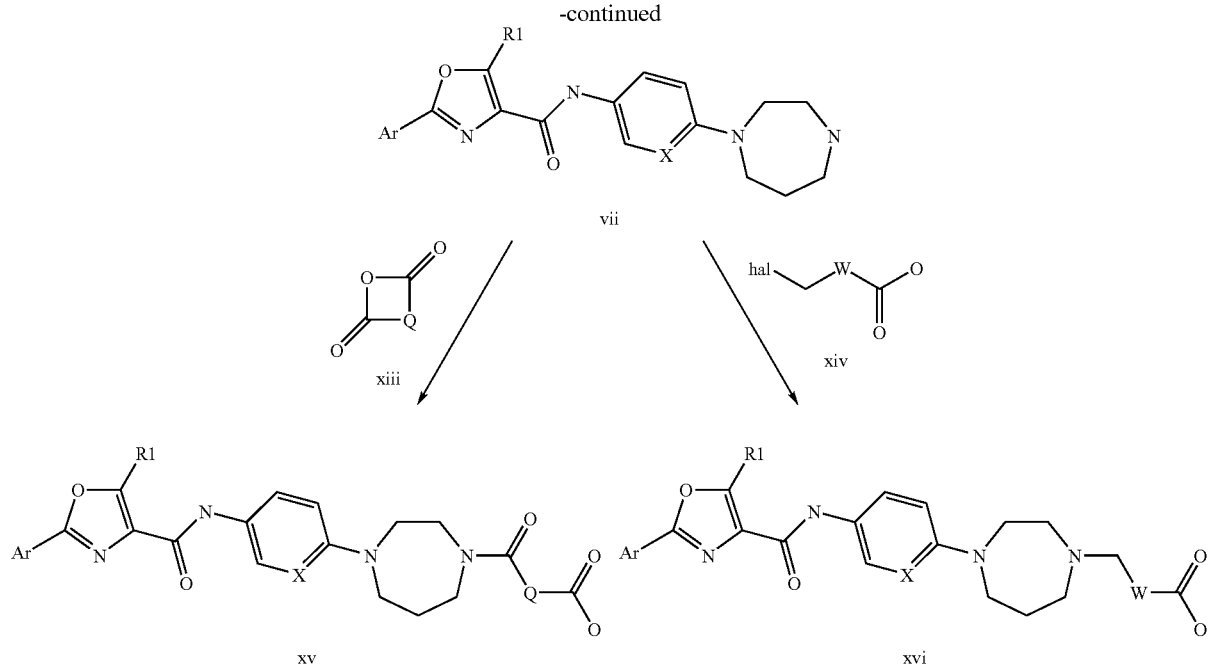

The preparation of desired DGAT inhibitors from the intermediate compound (vii) is illustrated in Scheme 2. Compound (vii) can react with acid chloride to form a corresponding amide (viii), where R2 can be alkyl or cycloalkyl group, R2 can also be heterocycle substituted lower alkyl group.

Alternatively, compound (vii) can also be reacted with alkoxycarbonyl chloride to form a carbamate (ix), where R3 can be lower alkyl or lower cycloalkyl.

The reaction of compound (vii) with an isocyanate can produce an urea (x), where R4 can be lower alkyl or lower cycloalkyl group.

The reaction of compound (vii) with a di-carboxylic acid derivative (xi) under amide formation conditions such as coupling reagents followed by the deprotection of the ester group can produce a corresponding carboxylic acid (xii), where E can be lower alkyl, or cycloalkyl group, and R5 can be methyl, ethyl or benzyl group. In the case where E is a cycloalkyl group, both cis- and trans-isomers can be prepared from the corresponding cis- or tran-carboxylic acids. The deprotection of the ester group R5 can be achieved through saponification (when R5 is methyl or ethyl group) or hydrogenation (when R5 is benzyl group).

Alternatively, carboxylic acid (xv) can be prepared by reacting compound (vii) with a cyclic anhydride (xiii), where Q can be lower alkyl or lower cycloalkyl group.

Finally, the direct alkylation of compound (vii) with an alkyl halide substituted carboxylic acid (xiv) can produce compound (xvi), where hal stands for halogen, such as chloride or bromide, and W can be aromatic or substituted aromatic ring.

The invention will now be further described in the Examples below, which are intended as an illustration only and do not limit the scope of the invention.

EXAMPLES

List of Abbreviations/Definitions

DGAT is diacylglycerol; acyl CoA O-acyltransferase
THF is tetrahydrofuran
DIC is N,N'-dicyclohexylcarbodiimide
DMF is N,N-dimethylformamide
DMA is N,N-dimethylacetamide
DMSO is dimethylsulfoxide
DCM is dichloromethane
DME is dimethoxyethane
NMP is N-methylpyrrolidine
MeOH is methanol
EtOH is ethanol
EtOAc is ethyl acetate
NBS is N-Bromosuccinimide
TFA is 1,1,1-trifluoroacetic acid
HOBT is 1-hydroxybenzotriazole
HBTU is O-(benzotriazol-yl)-N,N,N',N'-tetramethyluronium hexafluorophosphate
BOP is (benzotriazol-1-yloxy)tris(dimethylamino)phosphonium hexafluorophosphate
BOPCI is bis(2-oxo-3-oxazolidinyl)phosphinic chloride
PyBroP is bromotripyrrolidinophosphonium hexafluorophosphate
EDCI is 1-[3-(dimethylamino)propyl]-3-ethylcarbodiimide hydrochloride
DIPEA is N,N-diisopropylethylamine
Brine is saturated aqueous solution of sodium chloride
DAG is 1,2-dioleoyl-sn-glycerol
TLC is thin layer chromatography
RP HPLC is reversed phase high performance liquid chromatography
HRMS is high resolution mass spectrometry
LRMS is low resolution mass spectrometry APCI-MS is atmospheric pressure chemical ionization mass spectrometry
ES-MS is electrospray mass spectrometry
LCMS is liquid chromatography mass spectrometry
RT is room or ambient temperature.

Part I

Preferred Intermediates 4-(4-Nitro-phenyl)-[1,4]diazepane-1-carboxylic acid tert-butyl ester

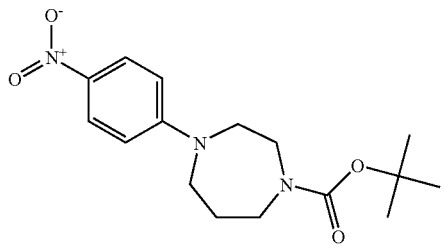

This compound was prepared in a similar way as described in literature (Journal of Medicinal Chemistry (2005), 48, 2371). A mixture of 1-fluoro-4-nitro-benzene (2.06 g, 14.7 mmol), [1,4]Diazepane-1-carboxylic acid tert-butyl ester (3.52 g, 17.6 mmol) and potassium carbonate (4.85 g, 35.2 mmol) in DMF (100 mL) was heated to 100° C. and stirred for 2 h. The reaction mixture was diluted with EtOAc (100 mL) and washed with water (100 mL), brine (50 mL), dried with anhydrous sodium sulfate and the solvent was removed. The residue was purified on a flash chromatography column with EtOAc/hexanes to afford 4-(4-nitrophenyl)-[1,4]diazepane-1-carboxylic acid tert-butyl ester (3.66 g, 78% yield) as a white solid. ES-MS for $C_{16}H_{23}N_3O_4$ calcd. (m/e) 321, observed 322 (M+H).

4-(5-Nitro-pyridin-2-yl)-[1,4]diazepane-1-carboxylic acid tert-butyl ester

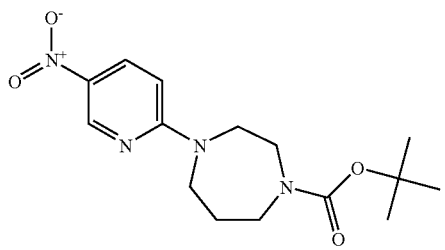

With a method similar to that used for the preparation of 4-(4-nitro-phenyl)-[1,4]diazepane-1-carboxylic acid tert-butyl ester above, 4-(5-nitro-pyridin-2-yl)-[1,4]diazepane-1-carboxylic acid tert-butyl ester was prepared from 2-chloro-5-nitro-pyridine and [1,4]Diazepane-1-carboxylic acid tert-butyl ester. ES-MS for $C_{15}H_{22}N_4O_4$ calcd. (m/e) 322, observed 323 (M+H).

4-(4-Amino-phenyl)-[1,4]diazepane-1-carboxylic acid tert-butyl ester

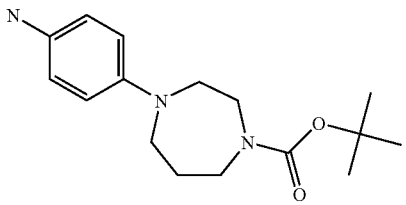

4-(4-Nitro-phenyl)-[1,4]diazepane-1-carboxylic acid tert-butyl ester (3.6 g) was diluted with ethanol (50 mL) and 10% Pd/C (400 mg) was added. The mixture was placed on a Parr shaker for hydrogenation at 50 psi for 3 hr The mixture was filtered and the solvent was removed to afford 4-(4-amino-phenyl)-[1,4]diazepane-1-carboxylic acid tert-butyl ester (3.2 g, 99% yield) as amorphous purple semi-solid. ES-MS for $C_{16}H_{25}N_3O_2$ calcd. (m/e) 291, observed 292 (M+H).

4-(5-Amino-pyridin-2-yl)-[1,4]diazepane-1-carboxylic acid tert-butyl ester

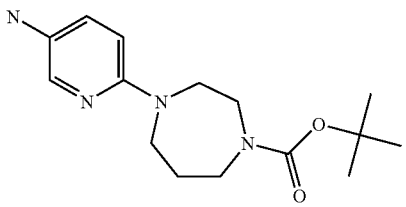

With a method similar to that used for the preparation of 4-(4-amino-phenyl)-[1,4]diazepane-1-carboxylic acid tert-butyl ester above, 4-(5-amino-pyridin-2-yl)-[1,4]diazepane-1-carboxylic acid tert-butyl ester was prepared from 4-(5-nitro-pyridin-2-yl)-[1,4]diazepane-1-carboxylic acid tert-butyl ester. ES-MS for $C_{15}H_{24}N_4O_2$ calcd. (m/e) 292, observed 293 (M+H).

4-{4-[(2-Phenyl-5-trifluoromethyl-oxazole-4-carbonyl)amino]phenyl}-[1,4]diazepane-1-carboxylic acid tert-butyl ester

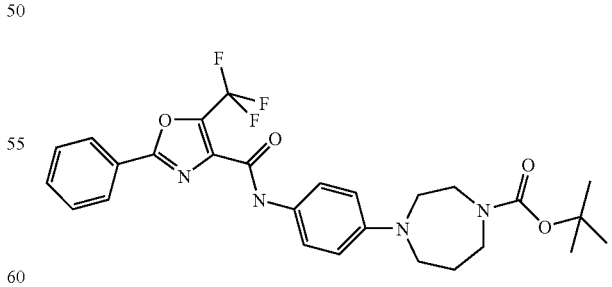

A mixture of 2-phenyl-5-trifluoromethyl-oxazole-4-carboxylic acid (1.0 g, 3.90 mmol), methylene chloride (50 mL), and a catalytic amount of DMF was stirred under argon, and oxalyl chloride (2M in methylene chloride, 2 mL, 4.0 mmol) was dripped into the mixture over 5 min. The mixture was stirred at room temperature for 1.0 hr and the reaction was concentrated to dryness. Benzene was added and the solution was evaporated to dryness again. The white-yellow solid was re-dissolved in methylene chloride (30 mL) and dripped, under argon, into a solution of 4-(4-amino-phenyl)-[1,4]diazepane-1-carboxylic acid tert-butyl ester (1.2 g, 4.0 mmol), and triethylamine (0.6 g, 5.8 mmol) in methylene chloride (50 mL). The reaction was stirred at room temperature for 0.5 hr then concentrated and the residue was taken up in EtOAc (100 mL) and washed with saturated ammonium chloride (100 mL), brine (100 mL) and dried with anhydrous sodium sulfate. The solvent was removed and the residue was purified on a flash column chromatography with EtOAc/hexanes to afford 4-{4-[(2-phenyl-5-trifluoromethyl-oxazole-4-carbonyl)-amino]-phenyl}-[1,4]diazepane-1-carboxylic acid tert-butyl ester (1.65 g, 83% yield) as a white solid. ES-MS for $C_{27}H_{29}F_3N_4O_4$ calcd. (m/e) 530, observed 531 (M+H).

4-{5-[(2-Phenyl-5-trifluoromethyl-oxazole-4-carbonyl)amino]pyridin-2-yl}-[1,4]diazepane-1-carboxylic acid tert-butyl ester

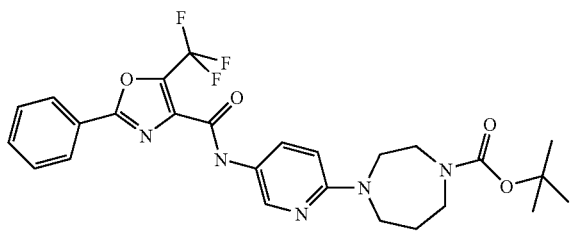

With a method similar to that used for the preparation of {4-[(2-phenyl-5-trifluoromethyl-oxazole-4-carbonyl)-amino]-phenyl}-[1,4]diazepane-1-carboxylic acid tert-butyl ester above, 4-{5-[(2-phenyl-5-trifluoromethyl-oxazole-4-carbonyl)amino]pyridin-2-yl}-[1,4]diazepane-1-carboxylic acid tert-butyl ester was prepared from 2-phenyl-5-trifluoromethyl-oxazole-4-carboxylic acid. ES-MS for $C_{26}H_{28}F_3N_5O_4$ calcd. (m/e) 531, observed 532 (M+H).

2-Phenyl-5-trifluoromethyl-oxazole-4-carboxylic acid (4-[1,4]diazepan-1-yl-phenyl)-amide hydrochloride

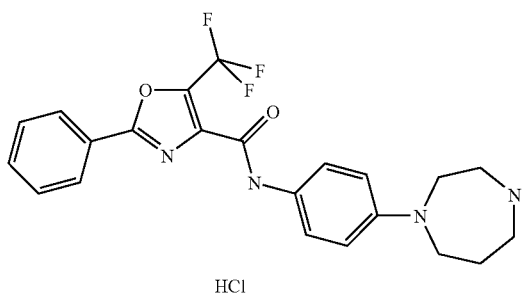

A mixture of 4-{4-[(2-Phenyl-5-trifluoromethyl-oxazole-4-carbonyl)-amino]-phenyl}-[1,4]diazepane-1-carboxylic acid tert-butyl ester (1.64 g, 3.1 mmol) in methanol (50 mL) and hydrogen chloride in dioxane (4M, 10 mL, 40 mmol) was stirred at room temperature for 24 hr. The solvents were removed under vacuum to yield 2-phenyl-5-trifluoromethyl-oxazole-4-carboxylic acid (4-[1,4]diazepan-1-yl-phenyl)-amide hydrochloride salt (1.57 g, 99% yield) as a white solid. ES-MS for the neutral form $C_{22}H_{21}F_3N_4O_2$ calcd. (m/e) 430, observed 431 (M+H).

2-Phenyl-5-trifluoromethyl-oxazole-4-carboxylic acid (6-[1,4]diazepan-1-yl-pyridin-3-yl)-amide hydrochloride

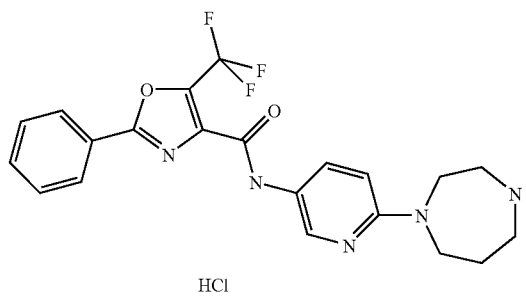

With a method similar to that used for the preparation of 2-phenyl-5-trifluoromethyl-oxazole-4-carboxylic acid (4-[1,4]diazepan-1-yl-phenyl)-amide hydrochloride above, 2-phenyl-5-trifluoromethyl-oxazole-4-carboxylic acid (6-[1,4]diazepan-1-yl-pyridin-3-yl)-amide hydrochloride was prepared from 4-{5-[(2-phenyl-5-trifluoromethyl-oxazole-4-carbonyl)amino]pyridin-2-yl}-[1,4]diazepane-1-carboxylic acid tert-butyl ester. ES-MS for the neutral form $C_{21}H_{20}F_3N_5O_2$ calcd. (m/e) 431, observed 432 (M+H).

Part II

Preferred Compounds

Example 1

4-{4-[(2-Phenyl-5-trifluoromethyl-oxazole-4-carbonyl)amino]phenyl}-[1,4]diazepane-1-carboxylic acid tert-butyl ester

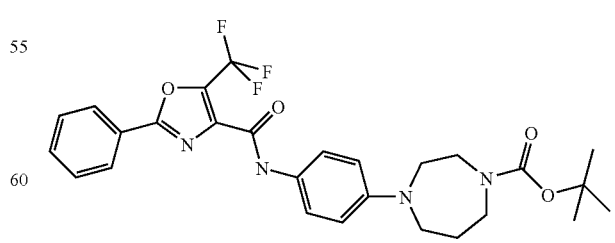

The preparation of this compound was described in the intermediate preparation section. ES-MS for $C_{27}H_{29}F_3N_4O_4$ calcd. (m/e) 530, observed 531 (M+H).

Example 2

4-{5-[(2-Phenyl-5-trifluoromethyl-oxazole-4-carbonyl)amino]pyridin-2-yl}-[1,4]diazepane-1-carboxylic acid tert-butyl ester

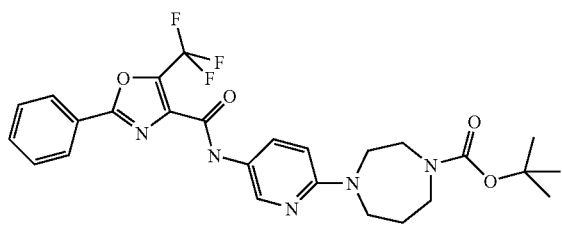

The preparation of this compound was described in the intermediate preparation section ES-MS for $C_{26}H_{28}F_3N_5O_4$ calcd. (m/e) 531, observed 532 (M+H).

Example 3

2,2-Dimethyl-4-oxo-4-(4-{4-[(2-phenyl-5-trifluoromethyl-oxazole-4-carbonyl)-amino]-phenyl}-[1,4]diazepan-1-yl)-butyric acid; hydrochloride

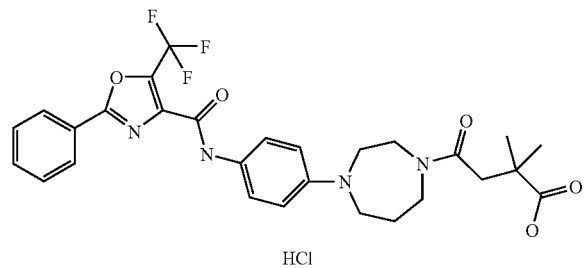

A mixture of 2-phenyl-5-trifluoromethyl-oxazole-4-carboxylic acid (4-[1,4]diazepan-1-yl-phenyl)-amide hydrochloride (35 mg, 0.075 mmol), methylene chloride (5 mL), and TEA (40 mg, 0.39 mmol) was stirred at room temperature. 2,2-Dimethylsuccinic anhydride (20 mg, 0.15 mmol) was added slowly. The reaction was stirred at room temperature for 0.5 hr then concentrated and the residue was taken up in ethyl acetate (50 mL) and washed with saturated ammonium chloride (50 mL), water (50 mL), and brine (20 mL). The solvent was removed and the residue was treated with hydrogen chloride in ether (1 N, 4 mL). The solid was filtered and washed with dry ether to afford 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid hydrochloride salt (35 mg, 85% yield). LCMS calcd for $C_{28}H_{29}F_3N_4O_5$ (m/e) 558, observed 559 (M+H).

Example 4

4-{4-[(2-Phenyl-5-trifluoromethyl-oxazole-4-carbonyl)-amino]-phenyl}-[1,4]diazepane-1-carboxylic acid ethyl ester; hydrochloride

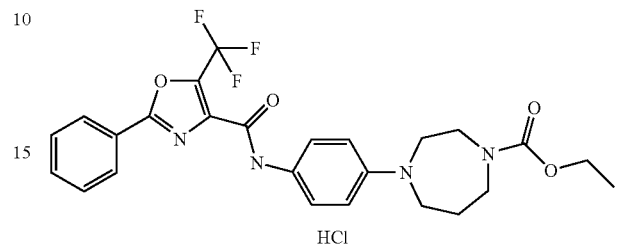

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid hydrochloride as described above, 4-{4-[(2-phenyl-5-trifluoromethyl-oxazole-4-carbonyl)-amino]-phenyl}-[1,4]diazepane-1-carboxylic acid ethyl ester was prepared from 2-phenyl-5-trifluoromethyl-oxazole-4-carboxylic acid (4-[1,4]diazepan-1-yl-phenyl)-amide hydrochloride and ethyl chloroformate. LCMS calcd for $C_{25}H_{25}F_3N_4O_4$ (m/e) 502, observed 503 (M+H).

Example 5

2-Phenyl-5-trifluoromethyl-oxazole-4-carboxylic acid [4-(4-cyclopropanecarbonyl-[1,4]diazepan-1-yl)-phenyl]-amide; hydrochloride

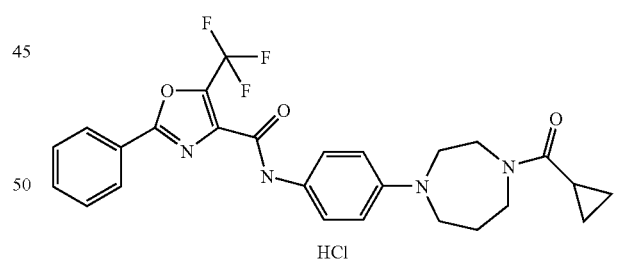

With a method similar to that used for the preparation of 2,2-dimethyl-4-oxo-4-(4-({4-[(2-phenyl-5-trifluoromethyl-oxazole-4-carbonyl)-amino]-phenyl}-[1,4]diazepan-1-yl)-butyric acid hydrochloride, 2-phenyl-5-trifluoromethyl-oxazole-4-carboxylic acid [4-(4-cyclopropanecarbonyl-[1,4]diazepan-1-yl)-phenyl]-amide hydrochloride was prepared from 2-phenyl-5-trifluoromethyl-oxazole-4-carboxylic acid (4-[1,4]diazepan-1-yl-phenyl)-amide hydrochloride and cyclopropane carbonyl chloride. LCMS calcd for $C_{26}H_{25}F_3N_4O_3$ (m/e) 498, observed 499 (M+H).

Example 6

4-{4-[(2-Phenyl-5-trifluoromethyl-oxazole-4-carbonyl)-amino]-phenyl}-[1,4]diazepane-1-carboxylic acid tert-butylamide

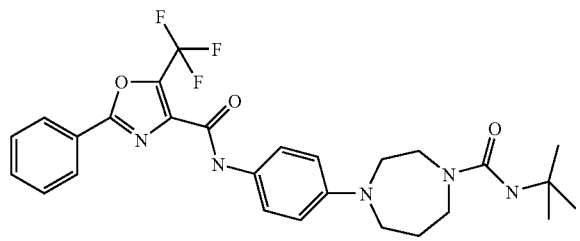

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, 4-{4-[(2-phenyl-5-trifluoromethyl-oxazole-4-carbonyl)-amino]-phenyl}-[1,4]diazepane-1-carboxylic acid tert-butylamide was prepared from 2-phenyl-5-trifluoromethyl-oxazole-4-carboxylic acid (4-[1,4]diazepan-1-yl-phenyl)-amide hydrochloride and tert-butyl isocyanate as a yellow solid after crystallization from ether. LCMS calcd for $C_{27}H_{30}F_3N_5O_3$ (m/e) 529, observed 530 (M+H).

Example 7

(E)-2-[2-Oxo-2-(4-{4-[(2-phenyl-5-trifluoromethyl-oxazole-4-carbonyl)-amino]-phenyl}-[1,4]diazepan-1-yl)-ethyl]-hex-3-enoic acid; hydrochloride

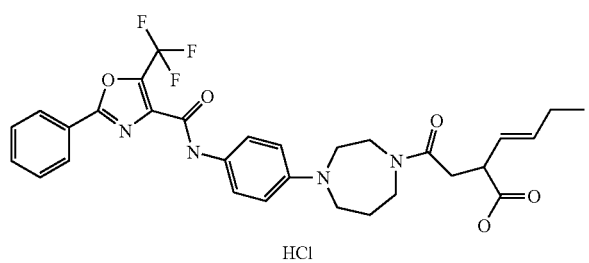

With a method similar to that used for the preparation of 2,2-dimethyl-4-oxo-4-(4-({4-[(2-phenyl-5-trifluoromethyl-oxazole-4-carbonyl)-amino]-phenyl}-[1,4]diazepan-1-yl)-butyric acid hydrochloride, (E)-2-[2-oxo-2-(4-{4-[(2-phenyl-5-trifluoromethyl-oxazole-4-carbonyl)-amino]-phenyl}-[1,4]diazepan-1-yl)-ethyl]-hex-3-enoic acid was prepared from 2-phenyl-5-trifluoromethyl-oxazole-4-carboxylic acid (4-[1,4]diazepan-1-yl-phenyl)-amide hydrochloride and ((E)-3-But-1-enyl)-dihydro-furan-2,5-dione. LCMS calcd for $C_{30}H_{31}F_3N_4O_5$ (m/e) 584, observed 585 (M+H).

Example 8

1-[2-Oxo-2-(4-{4-[(2-phenyl-5-trifluoromethyl-oxazole-4-carbonyl)-amino]-phenyl}-[1,4]diazepan-1-yl)-ethyl]-cyclopentanecarboxylic acid; hydrochloride

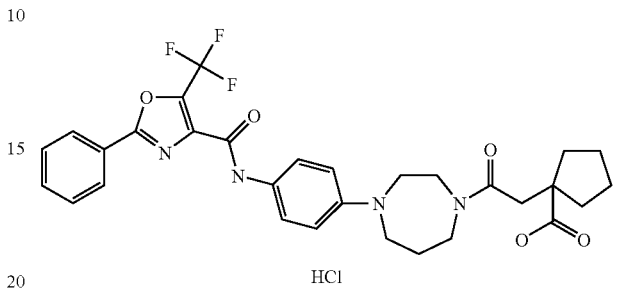

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid hydrochloride, 1-[2-oxo-2-(4-{4-[(2-phenyl-5-trifluoromethyl-oxazole-4-carbonyl)-amino]-phenyl}-[1,4]diazepan-1-yl)-ethyl]-cyclopentanecarboxylic acid was prepared from 2-phenyl-5-trifluoromethyl-oxazole-4-carboxylic acid (4-[1,4]diazepan-1-yl-phenyl)-amide hydrochloride and 2-oxa-spiro[4.4]nonane-1,3-dione. LCMS calcd for $C_{30}H_{31}F_3N_4O_5$ (m/e) 584, observed 585 (M+H).

Example 9

1-[2-Oxo-2-(4-{4-[(2-phenyl-5-trifluoromethyl-oxazole-4-carbonyl)-amino]-phenyl}-[1,4]diazepan-1-yl)-ethyl]-cyclohexanecarboxylic acid; hydrochloride

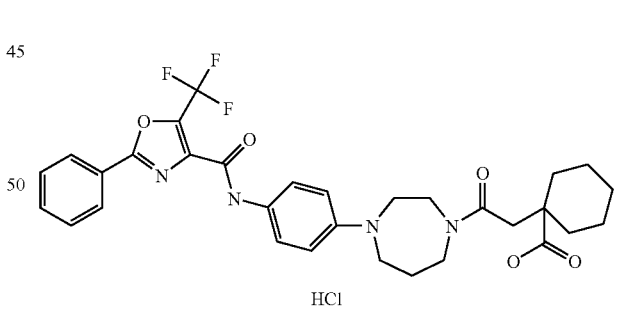

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid hydrochloride, 1-[2-oxo-2-(4-{4-[(2-phenyl-5-trifluoromethyl-oxazole-4-carbonyl)-amino]-phenyl}-[1,4]diazepan-1-yl)-ethyl]-cyclohexanecarboxylic acid was prepared from 2-phenyl-5-trifluoromethyl-oxazole-4-carboxylic acid (4-[1,4]diazepan-1-yl-phenyl)-amide hydrochloride and 2-oxa-spiro[4.5]decane-1,3-dione. LCMS calcd for $C_{31}H_{33}F_3N_4O_5$ (m/e) 598, observed 599 (M+H).

Example 10

2,2-Diethyl-4-oxo-4-(4-{4-[(2-phenyl-5-trifluoromethyl-oxazole-4-carbonyl)-amino]-phenyl}-[1,4]diazepan-1-yl)-butyric acid; hydrochloride

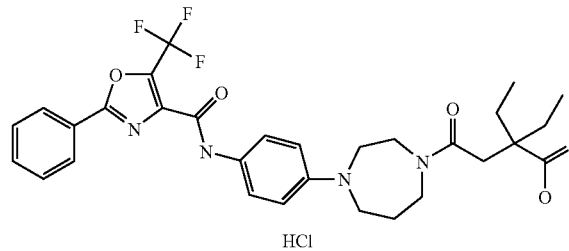

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid hydrochloride, 2,2-diethyl-4-oxo-4-(4-{4-[(2-phenyl-5-trifluoromethyl-oxazole-4-carbonyl)-amino]-phenyl}-[1,4]diazepan-1-yl)-butyric acid was prepared from 2-phenyl-5-trifluoromethyl-oxazole-4-carboxylic acid (4-[1,4]diazepan-1-yl-phenyl)-amide hydrochloride and 3,3-diethyl-dihydro-furan-2,5-dione. LCMS calcd for $C_{30}H_{33}F_3N_4O_5$ (m/e) 586, observed 587 (M+H).

Example 11

2-Phenyl-5-trifluoromethyl-oxazole-4-carboxylic acid [4-(4-cyclohexanecarbonyl-[1,4]diazepan-1-yl)-phenyl]-amide; hydrochloride

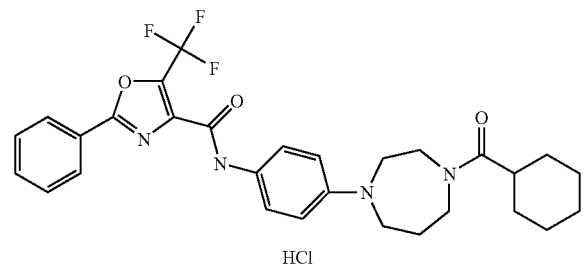

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid hydrochloride, 2-phenyl-5-trifluoromethyl-oxazole-4-carboxylic acid [4-(4-cyclohexanecarbonyl-[1,4]diazepan-1-yl)-phenyl-amide was prepared from 2-phenyl-5-trifluoromethyl-oxazole-4-carboxylic acid (4-[1,4]diazepan-1-yl-phenyl)-amide hydrochloride and cyclohexanecarbonyl chloride. LCMS calcd for $C_{29}H_{31}F_3N_4O_3$ (m/e) 540, observed 541 (M+H).

Example 12

2,2-Dimethyl-4-oxo-4-(4-{5-[(2-phenyl-5-trifluoromethyl-oxazole-4-carbonyl)-amino]-pyridin-2-yl}-[1,4]diazepan-1-yl)-butyric acid; hydrochloride

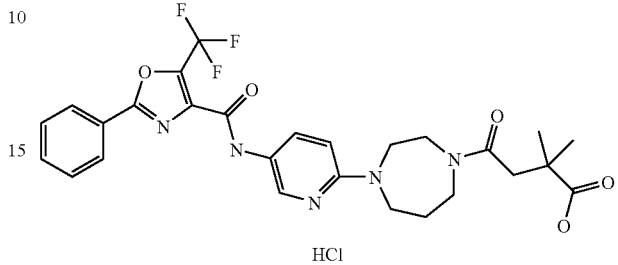

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid hydrochloride, 2,2-dimethyl-4-oxo-4-(4-{5-[(2-phenyl-5-trifluoromethyl-oxazole-4-carbonyl)-amino]-pyridin-2-yl}-[1,4]diazepan-1-yl)-butyric acid hydrochloride was prepared from 2-phenyl-5-trifluoromethyl-oxazole-4-carboxylic acid (6-[1,4]diazepan-1-yl-pyridin-3-yl)-amide hydrochloride and 2,2-dimethylsuccinic anhydride. LCMS for $C_{27}H_{28}F_3N_5O_5$ calcd. (m/e) 559, observed 560 (M+H).

Example 13

1-[2-Oxo-2-(4-{5-[(2-phenyl-5-trifluoromethyl-oxazole-4-carbonyl)-amino]-pyridin-2-yl}-[1,4]diazepan-1-yl)-ethyl]-cyclohexanecarboxylic acid

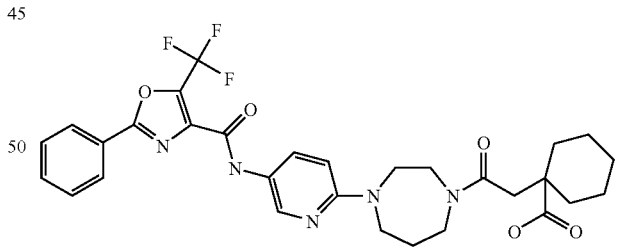

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, 1-[2-Oxo-2-(4-{5-[(2-phenyl-5-trifluoromethyl-oxazole-4-carbonyl)-amino]-pyridin-2-yl}-[1,4]diazepan-1-yl)-ethyl]-cyclohexanecarboxylic acid was prepared from 2-phenyl-5-trifluoromethyl-oxazole-4-carboxylic acid (6-[1,4]diazepan-1-yl-pyridin-3-yl)-amide hydrochloride and 2-oxa-spiro[4.5]decane-1,3-dione. LCMS for $C_{30}H_{32}F_3N_5O_5$ calcd. (m/e) 599, observed 600 (M+H).

Example 14

2,2-Diethyl-4-oxo-4-(4-{5-[(2-phenyl-5-trifluoromethyl-oxazole-4-carbonyl)-amino]-pyridin-2-yl}-[1,4]diazepan-1-yl)-butyric acid

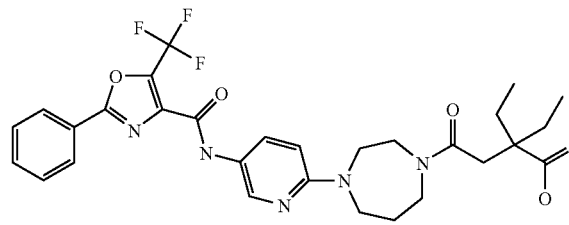

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, 2,2-diethyl-4-oxo-4-(4-{5-[(2-phenyl-5-trifluoromethyl-oxazole-4-carbonyl)-amino]-pyridin-2-yl}-[1,4]diazepan-1-yl)-butyric acid was prepared from 2-phenyl-5-trifluoromethyl-oxazole-4-carboxylic acid (6-[1,4]diazepan-1-yl-pyridin-3-yl)-amide hydrochloride and 3,3-diethyl-dihydro-furan-2,5-dione. LCMS for $C_{29}H_{32}F_3N_5O_5$ calcd. (m/e) 587, observed 588 (M+H).

Example 15

4-{5-[(2-Phenyl-5-trifluoromethyl-oxazole-4-carbonyl)-amino]-pyridin-2-yl}-[1,4]diazepane-1-carboxylic acid ethyl ester; hydrochloride

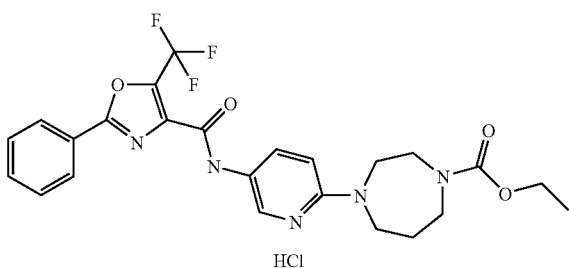

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, 4-{5-[(2-Phenyl-5-trifluoromethyl-oxazole-4-carbonyl)-amino]-pyridin-2-yl}-[1,4]diazepane-1-carboxylic acid ethyl ester was prepared from 2-phenyl-5-trifluoromethyl-oxazole-4-carboxylic acid (6-[1,4]diazepan-1-yl-pyridin-3-yl)-amide hydrochloride and ethyl chloroformate. LCMS for $C_{24}H_{24}F_3N_5O_4$ calcd. (m/e) 503, observed 504 (M+H).

Example 16

(E)-2-[2-Oxo-2-(4-{5-[(2-phenyl-5-trifluoromethyl-oxazole-4-carbonyl)-amino]-pyridin-2-yl}-[1,4]diazepan-1-yl)-ethyl]-hex-3-enoic acid; hydrochloride

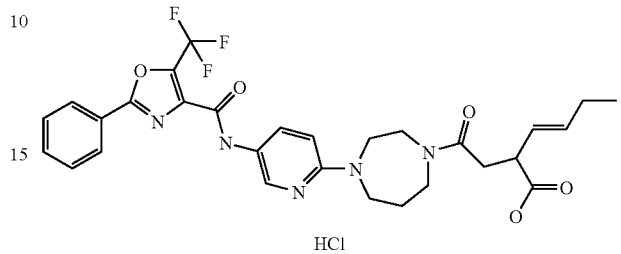

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, (E)-2-[2-Oxo-2-(4-{5-[(2-phenyl-5-trifluoromethyl-oxazole-4-carbonyl)-amino]-pyridin-2-yl}-[1,4]diazepan-1-yl)-ethyl]-hex-3-enoic acid was prepared from 2-phenyl-5-trifluoromethyl-oxazole-4-carboxylic acid (6-[1,4]diazepan-1-yl-pyridin-3-yl)-amide hydrochloride and ((E)-3-But-1-enyl)-dihydro-furan-2,5-dione. LCMS for $C_{29}H_{30}F_3N_5O_5$ calcd. (m/e) 585, observed 586 (M+H).

Example 17

2-Phenyl-5-trifluoromethyl-oxazole-4-carboxylic acid [6-(4-cyclohexanecarbonyl-[1,4]diazepan-1-yl)-pyridin-3-yl]-amide; hydrochloride

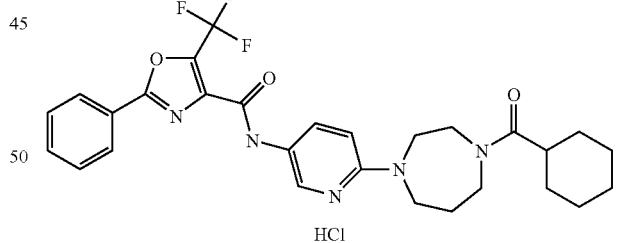

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, 2-Phenyl-5-trifluoromethyl-oxazole-4-carboxylic acid [6-(4-cyclohexanecarbonyl-[1,4]diazepan-1-yl)-pyridin-3-yl-amide was prepared from 2-phenyl-5-trifluoromethyl-oxazole-4-carboxylic acid (6-[1,4]diazepan-1-yl-pyridin-3-yl)-amide hydrochloride and cyclohexanecarbonyl chloride. LCMS for $C_{28}H_{30}F_3N_5O_3$ calcd. (m/e) 541, observed 542 (M+H).

Example 18

1-[2-Oxo-2-(4-{5-[(2-phenyl-5-trifluoromethyl-oxazole-4-carbonyl)-amino]-pyridin-2-yl}-[1,4]diazepan-1-yl)-ethyl]-cyclopentanecarboxylic acid

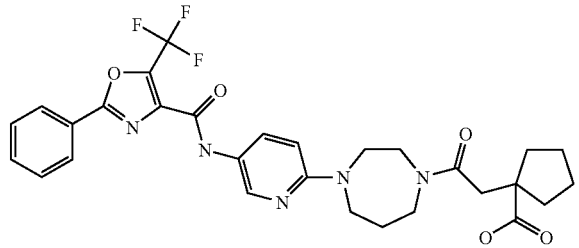

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, 1-[2-Oxo-2-(4-{5-(2-phenyl-5-trifluoromethyl-oxazole-4-carbonyl)-amino]-pyridin-2-yl}-[1,4]diazepan-1-yl)-ethyl]-cyclopentanecarboxylic acid was prepared from 2-phenyl-5-trifluoromethyl-oxazole-4-carboxylic acid (6-[1,4]diazepan-1-yl-pyridin-3-yl)-amide hydrochloride and 2-oxa-spiro[4.4]nonane-1,3-dione. LCMS for $C_{29}H_{30}F_3N_5O_5$ calcd. (m/e) 585, observed 586 (M+H).

Example 19

3,3-Dimethyl-5-oxo-5-(4-{5-[(2-phenyl-5-trifluoromethyl-oxazole-4-carbonyl)-amino]-pyridin-2-yl}-[1,4]diazepan-1-yl)-pentanoic acid; hydrochloride

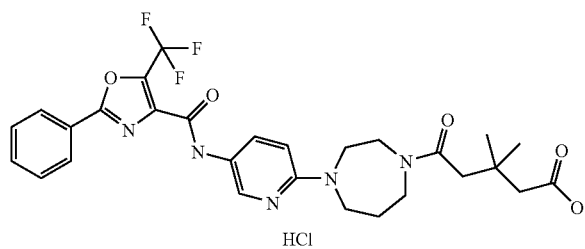

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, 3,3-Dimethyl-5-oxo-5-(4-{5-[(2-phenyl-5-trifluoromethyl-oxazole-4-carbonyl)-amino]-pyridin-2-yl}-[1,4]diazepan-1-yl)-pentanoic acid was prepared from 2-phenyl-5-trifluoromethyl-oxazole-4-carboxylic acid (6-[1,4]diazepan-1-yl-pyridin-3-yl)-amide hydrochloride and 4,4-dimethyl-dihydro-pyran-2,6-dione. LCMS for $C_{28}H_{30}F_3N_5O_5$ calcd. (m/e) 573, observed 574 (M+H).

Example 20

Cis-4-(4-{(4-[(2-Phenyl-5-trifluoromethyl-oxazole-4-carbonyl)-amino]-phenyl}-[1,4]diazepane-1-carbonyl)-cyclohexanecarboxylic acid benzyl ester

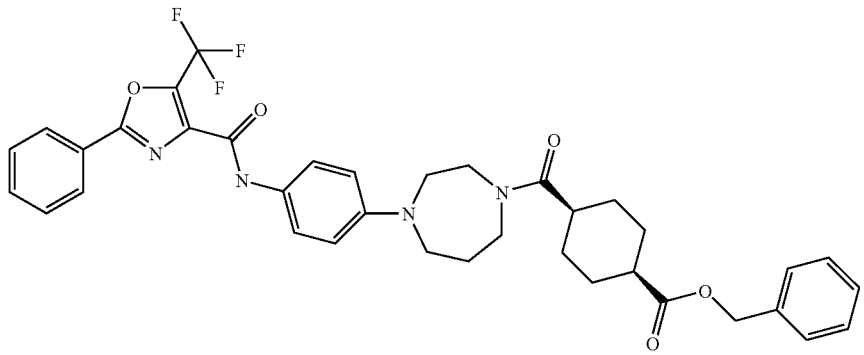

A mixture of 2-phenyl-5-trifluoromethyl-oxazole-4-carboxylic acid (4-[1,4]diazepan-1-yl-phenyl)-amide hydrochloride (100 mg, 0.21 mmol), cis-cyclohexane-1,4-dicarboxylic acid monobenzyl ester (0.67 mg, 0.25 mmol), and triethyl amine (0.070 mL) in DMF (5 mL) was stirred for 5 minutes and PyBroP (116 mg, 0.25 mmol) was added. The mixture was stirred at room temperature and after 1.0 hr the reaction was concentrated to dryness. The residue was extracted with ethyl acetate and washed with saturated ammonium chloride (100 mL), water (50 mL), brine (100 mL) and dried with anhydrous sodium sulfate. The solvent was removed and the crude material was purified on a flash column chromatography eluted with ethyl acetate/hexanes to afford cis-4-(4-{4-[(2-phenyl-5-trifluoromethyl-oxazole-4-carbonyl)-amino]-phenyl}-[1,4]diazepane-1-carbonyl)-cyclohexanecarboxylic acid benzyl ester (100 mg, 71% yield) as a white solid. LCMS for $C_{37}H_{37}F_3N_4O_5$ calcd. (m/e) 674, observed 675 (M+H).

Example 21

(1R,2R)-2-(4-{4-[(2-Phenyl-5-trifluoromethyl-oxazole-4-carbonyl)-amino]-phenyl}-[1,4]diazepane-1-carbonyl)-cyclopentanecarboxylic acid benzyl ester; hydrochloride

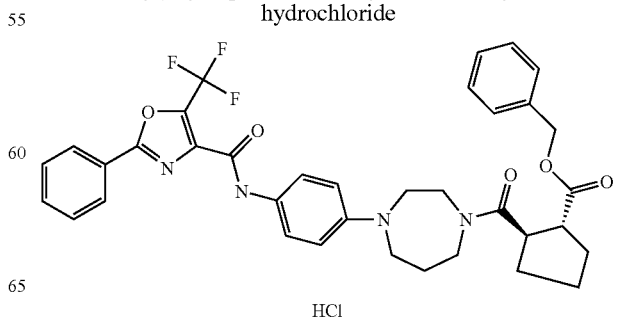

With a method similar to that used for the preparation of cis-4-(4-{4-[(2-phenyl-5-trifluoromethyl-oxazole-4-carbonyl)-amino]-phenyl}-[1,4]diazepane-1-carbonyl)-cyclohexanecarboxylic acid benzyl ester, (1R,2R)-2-(4-{4-[(2-phenyl-5-trifluoromethyl-oxazole-4-carbonyl)-amino]-phenyl}-[1,4]diazepane-1-carbonyl)-cyclopentanecarboxylic acid benzyl ester was prepared from 2-phenyl-5-trifluoromethyl-oxazole-4-carboxylic acid (4-[1,4]diazepan-1-yl-phenyl)-amide hydrochloride and (1R,2R)-cyclopentane-1,2-dicarboxylic acid monobenzyl ester. LCMS for $C_{36}H_{35}F_3N_4O_5$ calcd. (m/e) 660, observed 661 (M+H).

Example 22

2-Phenyl-5-trifluoromethyl-oxazole-4-carboxylic acid (4-{4-[2-(2,4-dioxo-thiazolidin-5-yl)-acetyl]-[1,4]diazepan-1-yl}-phenyl)-amide; hydrochloride

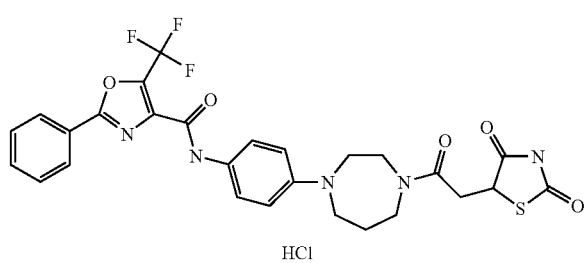

With a method similar to that used for the preparation of cis-4-(4-{4-[(2-phenyl-5-trifluoromethyl-oxazole-4-carbonyl)-amino]-phenyl}-[1,4]diazepane-1-carbonyl)-cyclohexanecarboxylic acid benzyl ester, 2-phenyl-5-trifluoromethyl-oxazole-4-carboxylic acid (4-{4-[2-(2,4-dioxo-thiazolidin-5-yl)-acetyl]-[1,4]diazepan-1-amide was prepared from 2-phenyl-5-trifluoromethyl-oxazole-4-carboxylic acid (4-[1,4]diazepan-1-yl-phenyl)-amide hydrochloride and (2,4-dioxo-thiazolidin-5-yl)-acetic acid. LCMS for $C_{27}H_{24}F_3N_5O_5S$ calcd. (m/e) 587, observed 588 (M+H).

Example 23

Cis-4-(4-{4-[(2-Phenyl-5-trifluoromethyl-oxazole-4-carbonyl)-amino]-phenyl}-[1,4]diazepane-1-carbonyl)-cyclohexanecarboxylic acid

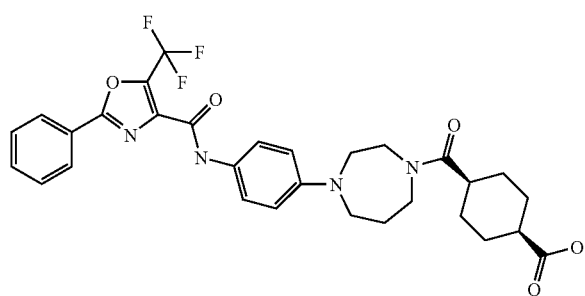

Cis-4-(4-{4-[(2-Phenyl-5-trifluoromethyl-oxazole-4-carbonyl)-amino]-phenyl}-[1,4]diazepane-1-carbonyl)-cyclohexanecarboxylic acid benzyl ester (90 mg) was diluted in 30 mL of methanol and 100 mg of Pd/C (10%) was added. The mixture was placed on a Parr shaker for hydrogenation at 50 psi for 3 hr. The mixture was filtered and the solvent was removed to afford the product 4-(4-{4-[(2-phenyl-5-trifluoromethyl-oxazole-4-carbonyl)-amino]-phenyl}-[1,4]diazepane-1-carbonyl)-cyclohexanecarboxylic acid (30 mg, 40% yield) as a white solid. LCMS for $C_{30}H_{31}F_3N_4O_5$ calcd. (m/e) 584, observed 585 (M+H).

Example 24

2-Phenyl-5-trifluoromethyl-oxazole-4-carboxylic acid {6-[4-(3,3-dimethyl-butyryl)-[1,4]diazepan-1-yl]-pyridin-3-yl}-amide; hydrochloride

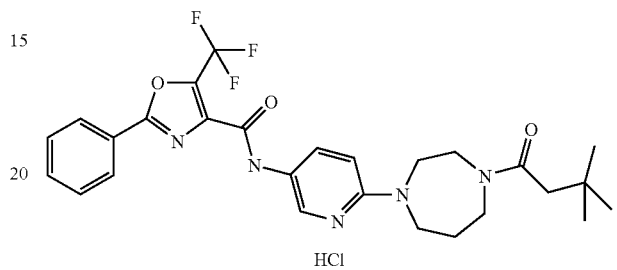

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, 2-phenyl-5-trifluoromethyl-oxazole-4-carboxylic acid {6-[4-(3,3-dimethyl-butyryl)-[1,4]diazepan-1-yl]-pyridin-3-yl}-amide was prepared from 2-phenyl-5-trifluoromethyl-oxazole-4-carboxylic acid (6-[1,4]diazepan-1-yl-pyridin-3-yl)-amide hydrochloride and 3,3-dimethyl-butyryl chloride. LCMS for $C_{27}H_{30}F_3N_5O_3$ calcd. (m/e) 529, observed 530 (M+H).

Example 25

4-{5-[(2-Phenyl-5-trifluoromethyl-oxazole-4-carbonyl)-amino]-pyridin-2-yl}-[1,4]diazepane-1-carboxylic acid methyl ester; hydrochloride

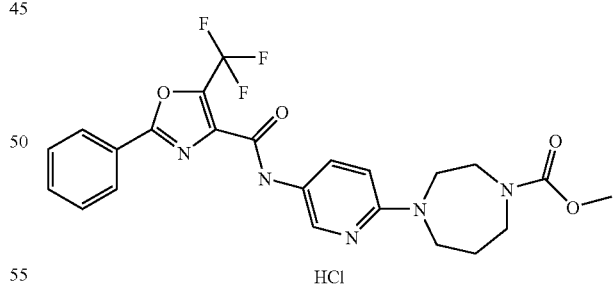

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, 4-{5-[(2-phenyl-5-trifluoromethyl-oxazole-4-carbonyl)-amino]-pyridin-2-yl}-[1,4]diazepane-1-carboxylic acid methyl ester was prepared from 2-phenyl-5-trifluoromethyl-oxazole-4-carboxylic acid (6-[1,4]diazepan-1-yl-pyridin-3-yl)-amide hydrochloride and methyl chloroformate. LCMS for $C_{23}H_{22}F_3N_5O_4$ calcd. (m/e) 489, observed 490 (M+H).

Example 26

2-Phenyl-5-trifluoromethyl-oxazole-4-carboxylic acid [6-(4-cyclopropanecarbonyl-[1,4]diazepan-1-yl)-pyridin-3-yl]-amide; hydrochloride

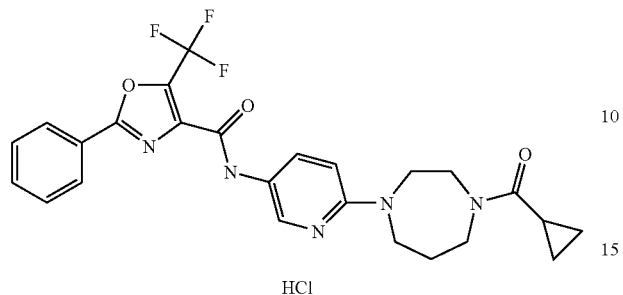

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, 2-phenyl-5-trifluoromethyl-oxazole-4-carboxylic acid [6-(4-cyclopropanecarbonyl-[1,4]diazepan-1-yl)-pyridin-3-yl]-amide was prepared from 2-phenyl-5-trifluoromethyl-oxazole-4-carboxylic acid (6-[1,4]diazepan-1-yl-pyridin-3-yl)-amide hydrochloride and cyclopropane carbonyl chloride. LCMS for $C_{25}H_{24}F_3N_5O_3$ calcd. (m/e) 499, observed 500 (M+H).

Example 27

3-[(4-{5-[(2-Phenyl-5-trifluoromethyl-oxazole-4-carbonyl)-amino]-pyridin-2-yl}-[1,4]diazepane-1-carbonyl)-amino]-propionic acid ethyl ester

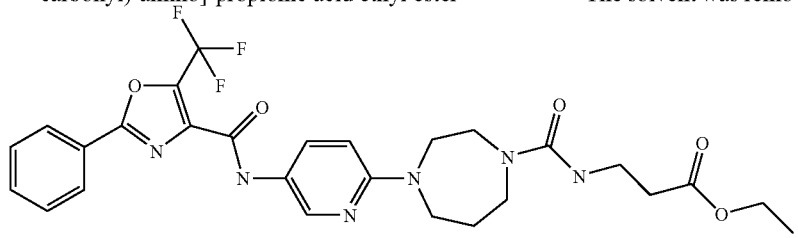

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, 3-[(4-{5-[(2-phenyl-5-trifluoromethyl-oxazole-4-carbonyl)-amino]-pyridin-2-yl}-[1,4]diazepane-1-carbonyl)-amino]-propionic acid ethyl ester was prepared from 2-phenyl-5-trifluoromethyl-oxazole-4-carboxylic acid (6-[1,4]diazepan-1-yl-pyridin-3-yl)-amide hydrochloride and 3-isocyanato-propionic acid ethyl ester. LCMS for $C_{27}H_{29}F_3N_6O_5$ calcd. (m/e) 574, observed 575 (M+H).

Example 28

4-{5-[(2-Phenyl-5-trifluoromethyl-oxazole-4-carbonyl)-amino]-pyridin-2-yl}-[1,4]diazepane-1-carboxylic acid isopropyl ester; hydrochloride

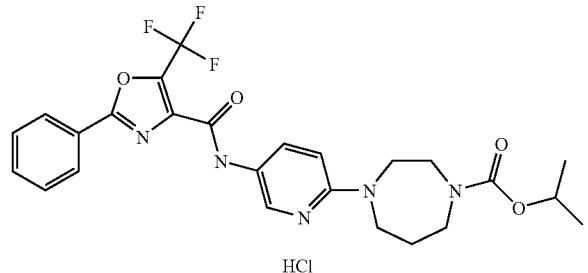

With a method similar to that used for the preparation of 2,2-dimethyl-4-oxo-4-(4-{4-[(2-phenyl-5-trifluoromethyl-oxazole-4-carbonyl)-amino]-phenyl}-[1,4]diazepan-1-yl)-butyric acid, 4-{5-[(2-phenyl-5-trifluoromethyl-oxazole-4-carbonyl)-amino]-pyridin-2-yl}-[1,4]diazepane-1-carboxylic acid isopropyl ester was prepared from 2-phenyl-5-trifluoromethyl-oxazole-4-carboxylic acid (6-[1,4]diazepan-1-yl-pyridin-3-yl)-amide hydrochloride and isopropyl chloroformate. LCMS for $C_{25}H_{26}F_3N_5O_4$ calcd. (m/e) 517, observed 518 (M+H).

Example 29

4-(4-{4-[(2-Phenyl-5-trifluoromethyl-oxazole-4-carbonyl)-amino]-phenyl}-[1,4]diazepan-1-ylmethyl)-benzoic acid

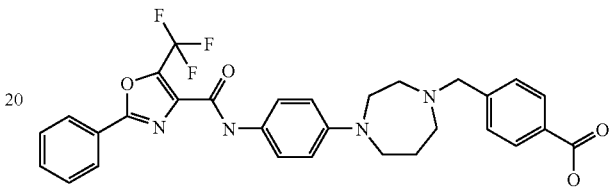

A mixture of 2-phenyl-5-trifluoromethyl-oxazole-4-carboxylic acid (4-[1,4]diazepan-1-yl-phenyl)-amide hydrochloride (56 mg, 0.12 mmol), 4-bromomethyl-benzoic acid (28 mg, 0.13 mmol), triethylamine (0.07 mL, 0.50 mmol) in DMF (5 mL) was stirred at room temperature for 0.5 hr then concentrated and the residue was taken up in 50 mL of ethyl acetate and washed with 50 mL of saturated ammonium chloride, water (50 mL), and dried with anhydrous sodium sulfate. The solvent was removed and the residue was triturated with ethyl acetate, followed by filtration, to afford 4-(4-{4-[(2-phenyl-5-trifluoromethyl-oxazole-4-carbonyl)-amino]-phenyl}-[1,4]diazepan-1-ylmethyl)-benzoic acid as a yellow solid (20 mg, 29% yield) LCMS for $C_{30}H_{27}F_3N_4O_4$ calcd. (m/e) 564, observed 565 (M+H).

Example 30

Trans-4-(4-{4-[(2-Phenyl-5-trifluoromethyl-oxazole-4-carbonyl)-amino]-phenyl}-[1,4]diazepane-1-carbonyl)-cyclohexanecarboxylic acid; hydrochloride

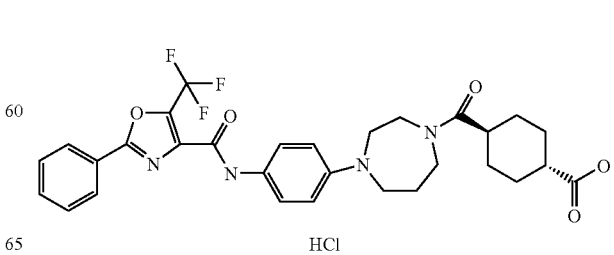

Trans-4-(4-{4-[(2-Phenyl-5-trifluoromethyl-oxazole-4-carbonyl)-amino]-phenyl-[1,4]diazepane-1-carbonyl)-cyclohexanecarboxylic acid benzyl ester (70 mg, prepared with the same method as the cis-isomer) was diluted in 30 mL of methanol and 100 mg of Pd/C (10%) was added. The mixture was placed on a Parr shaker for hydrogenation at 50 psi for 3 hr. The mixture was filtered and the solvent was removed. The residue was dried and then dissolved in ethyl acetate and treated with gaseous hydrogen chloride. Solvents were evaporated and the residue was triturated with ether and filtered to afford trans-4-(4-{4-[(2-phenyl-5-trifluoromethyl-oxazole-4-carbonyl)-amino]-phenyl}-[1,4]diazepane-1-carbonyl)-cyclohexanecarboxylic acid hydrochloride (50 mg, 74% yield) as a pale yellow solid. LCMS for $C_{30}H_{31}F_3N_4O_5$ calcd. (m/e) 584, observed 585 (M+H).

Example 31

(1R,2R)-2-(4-{4-[(2-Phenyl-5-trifluoromethyl-oxazole-4-carbonyl)-amino]-phenyl}-[1,4]diazepane-1-carbonyl)-cyclopentanecarboxylic acid; hydrochloride

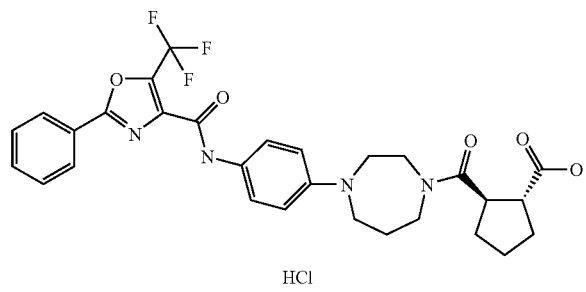

HCl

This compound was prepared through the hydrogenation of the corresponding benzyl ester (1R,2R)-2-(4-{4-[(2-phenyl-5-trifluoromethyl-oxazole-4-carbonyl)-amino]-phenyl}-[1,4]diazepane-1-carbonyl)-cyclopentanecarboxylic acid benzyl ester LCMS for $C_{29}H_{29}F_3N_4O_5$ calcd. (m/e) 570, observed 571 (M+H).

Example 32

DGAT Phospholipid FlashPlate Assay

Materials for the assay were: PL-FlashPlate: Phospholipid FlashPlates from PerkinElmer, catalog number SMP108; DAG (1,2-Dioleoyl-sn-glycerol) 10 mM suspended in water containing 0.1% Triton X-100; $^{14}$C-Pal-CoA (paimitoyl coenzyme A, [palmitoyl-1-$^{14}$C]) from PerkinElmer, catalog number NEC-555 with a specific activity of 55 mCi/mmol; and DGAT pellet, with a protein concentration of 9.85 mg/ml.

Aqueous buffers were prepared or purchased as follows: The coating buffer (CB) was purchased from, PerkinElmer, catalog number SMP900A; the reaction buffer (RB) was 50 mM Tris-HCl, pH 7.5, 100 mM NaCl, 0.01% BSA in water; the washing buffer (WB) was 50 mM Tris-HCl, pH 7.5, 100 mM NaCl, 0.05% deoxycholic acid sodium salt in water; the dilution buffer (DB) was 50 mM Tris-HCl, pH 7.5, 100 mM NaCl, 1 mM EDTA, 0.2% Triton X-100 in water.

1,2-Dioleoyl-sn-glycerol (DAG, 10 mmoles) was diluted to 500 µM with coating buffer (CB). The diluted DAG solution was then added to 384-well PL-FlashPlates at 60 µl per well, and incubated at room temperature for 2 days. The coated plates were then washed twice with washing buffer (WB) before use. Test compounds were serial diluted to 2000, 666.7, 222.2, 74.1, 24.7, 8.2, 2.7 and 0.9 µM in 100% DMSO. Diluted compound were further diluted 10 fold with reaction buffer (RB). $^{14}$C-Pal-CoA was diluted to 8.3 µM with RB. The DGAT pellet was diluted to 0.13 mg protein/ml with dilution buffer (DB) immediately before it was added to the PL-FlashPlates to start the reaction. 20 µl of the RB-diluted compounds (or 10% DMSO in RB for Total and Blank), 15 µl of RB diluted 14C-Pal-CoA and 15 µl of DB diluted DGAT pellet (DB without DGAT for Blanks) were transferred to each well of the PL-FlashPlates. The reaction mixtures were incubated at 37° C. for 1 hour. The reactions were stopped by washing 3 times with WB. Plates were sealed with Top-seal and read on a Topcount instrument.

Calculation of $IC_{50}$: The $IC_{50}$ values for each compound were generated using an Excel template. The Topcount rpm readings of Total and Blank were used as 0% and 100% inhibition. The percent inhibition values of reactions in the presence of compounds were calculated, and plotted against compound concentrations. All data were fitted into a Dose Response One Site model (4 parameter logistic model) as the following:

$$(A+((B-A)/(1+((x/C)^D)))),$$

while A and B as the bottom and top of the curve (highest and lowest inhibition), respectively, and C as $IC_{50}$ and D as Hill Coefficient of the compound. The results are presented in Table 1:

TABLE 1

| Example | IC50 (µM) in DGAT Phospholipid Flash Plate Assay |
|---------|--------------------------------------------------|
| 1 | 0.188 |
| 2 | 0.255 |
| 3 | 0.08 |
| 4 | 0.281 |
| 5 | 0.138 |
| 6 | 0.098 |
| 7 | 0.118 |
| 8 | 0.083 |
| 9 | 0.151 |
| 10 | 0.108 |
| 11 | 0.275 |
| 12 | 0.187 |
| 13 | 0.112 |
| 14 | 0.114 |
| 15 | 0.221 |
| 16 | 0.228 |
| 17 | 0.208 |
| 18 | 0.142 |
| 19 | 0.224 |
| 20 | 0.289 |
| 21 | 0.477 |
| 22 | 0.081 |
| 23 | 0.095 |
| 24 | 0.145 |
| 25 | 0.227 |
| 26 | 0.194 |
| 27 | 0.193 |
| 28 | 0.23 |
| 29 | 0.218 |
| 30 | 0.323 |
| 31 | 0.096 |

It is to be understood that the invention is not limited to the particular embodiments of the invention described above, as variations of the particular embodiments may be made and still fall within the scope of the appended claims.

What is claimed is:

1. A compound of formula (I):

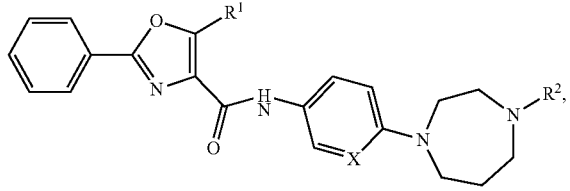

wherein:
X is CH or N;
R¹ is lower alkyl substituted with halogen;
R² is —CH₂-aryl, said aryl being unsubstituted or substituted with C(O)OH, or —C(O)—R³;
R³ is -lower alkyl, unsubstituted or substituted with carboxylic acid,
—O-lower alkyl, unsubstituted or substituted with C(O)OH,
—(CH₂)ₙ-cycloalkyl, said cycloalkyl being unsubstituted or substituted with C(O)OH or C(O)O—CH₂-phenyl,
—(CH₂)ₙ-aryl, said aryl being unsubstituted or mono- or bi-substituted with C(O)OH,
—NH-lower alkyl,
—(CH₂)ₙ-heterocycloalkyl, said heterocycloalkyl being unsubstituted or substituted with (=O), or —NH(CH₂)₂C(O)OCH₂CH₃; and
n is 0, 1 or 2;
or a pharmaceutically acceptable salt thereof.

2. The compound according to claim 1, wherein:
X is CH;
R¹ is —CF₃;
R² is —CH₂-aryl, said aryl being unsubstituted or substituted with C(O)OH, or —C(O)—R³;
R³ is —O-lower alkyl, unsubstituted or substituted with C(O)OH,
—(CH₂)ₙ-cycloalkyl, said cycloalkyl being unsubstituted or substituted with C(O)OH or C(O)O—CH₂-phenyl,
—(CH₂)ₙ-aryl, said aryl being unsubstituted or mono- or bi-substituted with C(O)OH,
—NH-lower alkyl,
—(CH₂)ₙ-heterocycloalkyl, said heterocycloalkyl being unsubstituted or substituted with (=O), or
—NH(CH₂)₂C(O)OCH₂CH₃; and
n is 0, 1 or 2.

3. The compound according to claim 1, wherein:
X is N;
R¹ is CF₃;
R² is —CH₂-aryl, said aryl being unsubstituted or substituted with C(O)OH, or —C(O)—R³;
R³ is —O-lower alkyl, unsubstituted or substituted with C(O)OH,
—(CH₂)ₙ-cycloalkyl, said cycloalkyl being unsubstituted or substituted with C(O)OH or C(O)O—CH₂-phenyl,
—(CH₂)ₙ-aryl, said aryl being unsubstituted or mono- or bi-substituted with C(O)OH,
—NH-lower alkyl,
—(CH₂)ₙ-heterocycloalkyl, said heterocycloalkyl being unsubstituted or substituted with (~0), or
—NH(CH₂)₂C(O)OCH₂CH₃; and
n is 0, 1 or 2.

4. The compound according to claim 1, wherein R² is —C(O)—R³.

5. The compound according to claim 1, wherein R³ is —OCH₃, —OC(CH₃)₃, —CH₂C(CH₃)₂C(O)OH, —OCH(CH₃)₂, —OCH₂CH₃, —NHC(CH₃)₃, —CH₂C(CH₃)₂CH₂C(O)OH, —CH₂CH(CH=CHCH₂CH₃)C(O)OH, —CH₂C(CH₃)₃, —NH(CH₂)₂C(O)OCH₂CH₃, —CH₂—CH₂C(CH₂CH₃)₂C(O)OH, cyclopentanecarboxylic acid, cyclohexane, cyclopropane, —CH₂-cyclohexanecarboxylic acid, cyclohexanecarboxylic acid, cyclohexanecarboxylic acid benzyl ester, cyclopentanecarboxylic acid benzyl ester, —CH₂-dioxothiazolidinyl, or —CH₂-benzoic acid.

6. The compound according to claim 1, wherein n is 0 or 1.

7. The compound according to claim 1, wherein said compound is:

2,2-dimethyl-4-oxo-4-(4-{4-[(2-phenyl-5-trifluoromethyl-oxazole-4-carbonyl)-amino]-phenyl}-[1,4]diazepan-1-yl)-butyric acid; hydrochloride, 2-phenyl-5-trifluoromethyl-oxazole-4-carboxylic acid [4-(4-cyclopropanecarbonyl-[1,4]diazepan-1-yl)-phenyl]-amide; hydrochloride, 4-{4-[(2-phenyl-5-trifluoromethyl-oxazole-4-carbonyl)-amino]-phenyl}[1,4]diazepane-1-carboxylic acid tert-butylamide, 1-[2-oxo-2-(4-{4-[(2-phenyl-5-trifluoromethyl-oxazole-4-carbonyl)-amino]-phenyl}-[1,4]diazepan-1-yl)-ethyl]-cyclopentanecarboxylic acid; hydrochloride, 2-phenyl-5-trifluoromethyl-oxazole-4-carboxylic acid (4-{4-[2-(2,4-dioxo-thiazolidin-5-yl)-acetyl]-[1,4]diazepan-1-yl}-phenyl)-amide; hydrochloride, cis-4-(4-{4-[(2-phenyl-5-trifluoromethyl-oxazole-4-carbonyl)-amino]-phenyl}-[1,4]diazepane-1-carbonyl)-cyclohexanecarboxylic acid, 4-{5-[(2-phenyl-5-trifluoromethyl-oxazole-4-carbonyl)-amino]-pyridin-2-yl}-[1,4]diazepane-1-carboxylic acid methyl ester; hydrochloride, 2-phenyl-5-trifluoromethyl-oxazole-4-carboxylic acid [6-(4-cyclopropanecarbonyl-[1,4]diazepan-1-yl)-pyridin-3-yl]-amide; hydrochloride, 4-{5-[(2-phenyl-5-trifluoromethyl-oxazole-4-carbonyl)-amino]-pyridin-2-yl}-[1,4]diazepane-1-carboxylic acid isopropyl ester; hydrochloride or (1R,2R)-2-(4-{4-[(2-phenyl-5-trifluoromethyl-oxazole-4-carbonyl)-amino]-phenyl}-[1,4]diazepane-1-carbonyl)-cyclopentanecarboxylic acid; hydrochloride.

8. A pharmaceutical composition, comprising a therapeutically effective amount of a compound according to claim 1 or a pharmaceutically acceptable salt thereof and a pharmaceutically acceptable carrier.

9. The compound of claim 2 wherein R² is —CH²-aryl and aryl is substituted or unsubstituted phenyl.

10. The compound of claim 3 wherein $R^2$ is —CH$_2$-aryl and aryl is substituted or unsubstituted phenyl.

11. The compound of claim 2 wherein $R^2$ is —C(O)—$R^3$ and $R^3$ is a monocyclic 5 to 7 membered substituted or unsubstituted heterocycloalkyl ring containing from 1 to 2 heteroatoms selected from the group consisting of N, O or S.

12. The compound of claim 3 wherein $R^2$ is —C(O)—$R^3$ and $R^3$ is a monocyclic 5 to 7 membered substituted or unsubstituted heterocycloalkyl ring containing from 1 to 2 heteroatoms selected from the group consisting of N, O or S.

13. The compound according to claim 1, wherein said compound is 2-phenyl-5-trifluoromethyl-oxazole-4-carboxylic acid {6-[4-(3,3-dimethyl-butyryl)-[1,4]diazepan-1-yl]-pyridin-3-yl}-amide; hydrochloride.

14. A pharmaceutical composition, comprising a therapeutically effective amount of a compound according to claim 7 or a pharmaceutically acceptable salt thereof and a pharmaceutically acceptable carrier.

15. A pharmaceutical composition, comprising a therapeutically effective amount of a compound according to claim 13 or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 8,211,884 B2  
APPLICATION NO. : 12/507890  
DATED : July 3, 2012  
INVENTOR(S) : David R. Bolin et al.

Page 1 of 1

It is certified that error appears in the above-identified patent and that said Letters Patent is hereby corrected as shown below:

Column 4, line 14, that portion reading "$NH(CH_2)_2C(O)OCH_2Ch_3$" should read  
--$NH(CH_2)_2C(O)OCH_2CH_3$--.

Claim 3, at column 34, line 5, that portion reading "substituted with (~0)" should read  
--substituted with (=O)--.

Claim 9, at column 34, line 66, that portion reading "wherein $R^2$ is –$CH^2$-aryl" should read  
--wherein $R^2$ is –$CH_2$-aryl--.

Signed and Sealed this  
Twenty-sixth Day of March, 2013

Teresa Stanek Rea  
*Acting Director of the United States Patent and Trademark Office*